United States Patent [19]

Neumann et al.

[11] 4,373,102
[45] Feb. 8, 1983

[54] ISOINDOLINE DYES, THEIR PREPARATION AND USE

[75] Inventors: Peter Neumann, Wiesloch; Wolfgang Elser, Wachenheim; Gustav Bock, Neustadt; Wolf-Dieter Kermer, Fussgoenheim, all of Fed. Rep. of Germany

[73] Assignee: BASF Aktiengesellschaft, Rheinland-Pfalz, Fed. Rep. of Germany

[21] Appl. No.: 128,156

[22] Filed: Mar. 7, 1980

[30] Foreign Application Priority Data

Mar. 29, 1979 [DE] Fed. Rep. of Germany ....... 2912428

[51] Int. Cl.³ ................. C07D 209/44; C07D 401/10; C07D 403/10; C07D 413/10
[52] U.S. Cl. ................... 544/143; 542/421; 544/63; 544/80; 544/96; 544/114; 544/121; 544/122; 544/129; 544/130; 544/137; 544/139; 544/140; 544/238; 544/333; 544/364; 544/373; 546/200; 548/215; 548/240; 548/300; 548/356; 8/649; 8/657; 106/288 Q; 544/232; 544/243; 544/337; 548/470
[58] Field of Search ................. 260/326.1; 544/63, 96, 544/143, 80, 238, 333, 373, 129, 130, 121, 122, 114, 137, 139, 140, 364, 232, 243, 337; 546/200; 548/215, 240, 300, 356; 542/421

[56] References Cited

U.S. PATENT DOCUMENTS 3,646,033 2/1972 Leister et al. .................... 260/250 C
3,706,525 12/1972 Blackwell et al. .................... 8/21 C
4,051,099 9/1977 von der Crone ............... 260/326.1

OTHER PUBLICATIONS

Micheel et al., Chem. Ber. 94, 1749 (1961).
Elser et al., Chem. Abs. 79, 20304m (1973).

*Primary Examiner*—Mark L. Berch
*Attorney, Agent, or Firm*—Oblon, Fisher, Spivak, McClelland & Maier

[57] ABSTRACT

Novel dyes of the formula

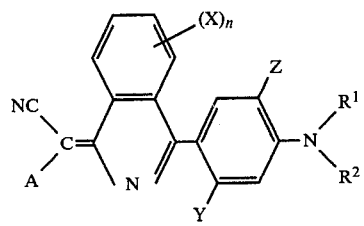

where
A is cyano, carbo-$C_1$-$C_4$-alkoxy, carbamyl, N-$C_1$-$C_4$-alkylcarbamyl, N-phenylcarbamyl, acetyl, benzoyl, 4-nitrophenyl or 4-cyanophenyl,
X is hydrogen, chlorine, $C_1$-$C_4$-alkyl or $C_1$-$C_4$-alkoxy, and if n is 2 the substituents may be identical or different,
n is 1 or 2,
$R^1$ is hydrogen, methyl, ethyl or 2-hydroxyethyl and
$R^2$ is phenyl or cyclohexyl, or
$R^1$ is hydrogen and
$R^2$ is $C_1$-$C_4$-alkyl, or
$R^1$ and $R^2$ are $C_1$-$C_6$-alkyl, allyl or phenyl-$C_1$-$C_4$-alkyl or
the group

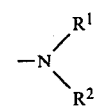

is a saturated heterocyclic five-membered or six-membered ring which may additionally contain an oxygen or a further nitrogen as ring members,
Y is hydrogen, hydroxyl, methyl or ethyl;

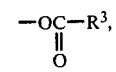

where $R^3$ is linear or branched $C_1$-$C_{12}$-alkyl, or is phenyl;

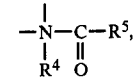

where $R^4$ is hydrogen or $C_1$-$C_4$-alkyl and $R^5$ is hydrogen, linear or branched $C_1$-$C_{12}$-alkyl or trifluoromethyl; chloromethyl; $C_1$-$C_4$-alkoxymethyl, phenoxymethyl, benzyl, phenylethyl, $C_3$-$C_7$-cycloalkyl, phenyl, $H_5C_6$—CH=CH— or —$CH_2$—$PO(OR^6)_2$, where $R^6$ is $C_1$-$C_4$-alkyl; or

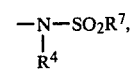

where $R^7$ is $C_1$-$C_{12}$-alkyl, phenyl or $C_1$-$C_{12}$-alkylphenyl; or Y is N-$C_1$-$C_4$-alkylamino if $R^1$ and $R^2$ are $C_1$-$C_4$-alkyl, or Y is N,N-di-$C_1$-$C_4$-alkylamino, N-pyrrolidinyl, N-piperidinyl or N-morpholinyl if

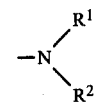

has the same meaning, and
Z is hydrogen or, if $R^1$ and $R^2$ are $C_1$-$C_4$-alkyl or allyl and Y is

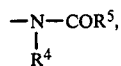

Z is hydrogen, methoxy or ethoxy, and
alkyl, phenyl, phenoxy and phenylthio may contain additional substituents.

The dyes give blue to violet hues on synthetics, in particular on linear polyester fibers. Where Z is methoxy or ethoxy, greenish blue dyeings are obtained. The dyeings are very deep, clear and brilliant.

Some of the dyes may also be used for the mass coloring of thermoplastics.

21 Claims, No Drawings

ISOINDOLINE DYES, THEIR PREPARATION AND USE

The present invention relates to novel dyes based on isoindolenine, to a process for the preparation of the dyes, and to their use.

The novel dyes have the general formula

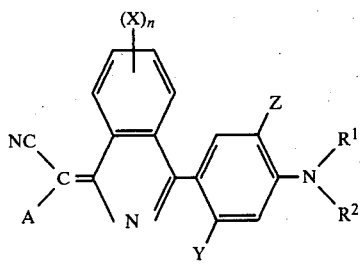

(I)

where

A is cyano, carbo-$C_1$-$C_4$-alkoxy, carbamyl, N-$C_1$-$C_4$-alkyl-carbamyl, where alkyl is unsubstituted or substituted by $C_1$-$C_4$-alkoxy, N-phenylcarbamyl, where phenyl is unsubstituted or substituted by $C_1$-$C_4$-alkyl or $C_1$-$C_4$-alkoxy, acetyl, benzoyl, 4-nitrophenyl or 4-cyanophenyl, X is hydrogen, chlorine, $C_1$-$C_4$-alkyl or $C_1$-$C_4$-alkoxy, and if n is 2 the substituents may be identical or different, n is 1 or 2, $R^1$ is hydrogen, methyl, ethyl or 2-hydroxyethyl and $R^2$ is phenyl which is unsubstituted or substituted by $C_1$-$C_4$-alkyl or $C_1$-$C_4$-alkoxy, or is cyclohexyl, or $R^1$ is hydrogen and $R^2$ is $C_1$-$C_4$-alkyl or $R^1$ and $R^2$ are $C_1$-$C_6$-alkyl; $C_1$-$C_4$-alkyl substituted by chlorine, cyano, hydroxyl, $C_1$-$C_4$-alkoxy, phenoxy, $C_2$-$C_5$-alkanoyloxy (which may or may not be substituted by $C_1$-$C_4$-alkoxy or phenoxy) or carbo-$C_1$-$C_4$-alkoxy; allyl; or phenyl-$C_1$-$C_4$-alkyl or

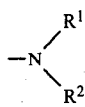

is a saturated heterocyclic five-membered or six-membered ring which may additionally contain an oxygen or a further nitrogen as a ring member, Y is hydrogen, hydroxyl, methyl or ethyl;

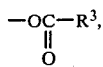

where $R^3$ is linear or branched $C_1$-$C_{12}$-alkyl or phenyl which is unsubstituted or substituted by $C_1$-$C_4$-alkyl or $C_1$-$C_4$-alkoxy;

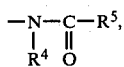

where $R^4$ is hydrogen or $C_1$-$C_4$-alkyl and $R^5$ is hydrogen, linear or branched $C_1$-$C_{12}$-alkyl, trifluoromethyl, chloromethyl, $C_1$-$C_4$-alkoxymethyl or phenoxymethyl (where phenoxy may or may not be substituted by one or two chlorine, methoxy, nitro or $C_1$-$C_4$-alkyl, and, in the case of two substituents, the substituents may be identical or different); phenylthiomethyl, where phenyl is unsubstituted or substituted by $C_1$-$C_4$-alkyl; benzyl; phenylethyl; $C_3$-$C_7$-cycloalkyl; phenyl which is unsubstituted or substituted by $C_1$-$C_{12}$-alkyl, $C_1$-$C_{12}$-alkoxy or nitro; $H_5C_6$—CH=CH—; —$CH_2$—$PO(OR^6)_2$, where $R^6$ is $C_1$-$C_4$-alkyl, or

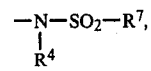

where $R^4$ has the above meanings and $R^7$ is $C_1$-$C_{12}$-alkyl, phenyl, or $C_1$-$C_{12}$-alkylphenyl, or Y is N—$C_1$-$C_4$-alkylamino, if $R^1$ and $R^2$ are $C_1$-$C_4$-alkyl or Y is N,N-di-$C_1$-$C_4$-alkylamino, N-pyrrolidinyl, N-piperidinyl or N-morpholinyl if

has the same meaning, and

Z is hydrogen or, if $R^1$ and $R^2$ are $C_1$-$C_4$-alkyl or allyl and Y is

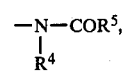

Z is hydrogen, methoxy or ethoxy.

The dyes dye synthetic materials, especially linear polyester fibers, in blue to violet hues from aqueous baths. Where Z is methoxy or ethoxy, greenish blue dyeings are obtained. The dyeings are very deep and in this respect are equal to or superior to those obtained with prior art dyes. The hues obtained are clear and brilliant, and are very fast to thermofixing. Some of the novel dyes may also be used for the mass coloring of thermoplastics, whilst others may be used for the dyeing process described in German Pat. No. 1,811,796. Here again, brilliant hues are obtained.

Suitable substituents A, in addition to acetyl, benzoyl, 4-nitrophenyl, 4-cyanophenyl, carbamyl and cyano, are:

(a) carbo-$C_1$-$C_4$-alkoxy, eg. carbomethoxy, carboethoxy, carbo-n-propoxy, carboisopropoxy, carbo-n-butoxy and carboisobutoxy;

(b) N-alkylcarbamyl, where alkyl may be unsubstituted or substituted, eg. N-methyl-, N-ethyl-, N-propyl-, N-butyl-, N-(3-methoxypropyl)-, N-(3-ethoxypropyl)-, N-(3-propoxypropyl)- and N-(3-butoxypropyl)-carbamyl;

(c) N-phenylcarbamyl, where phenyl is unsubstituted or substituted, eg. N-phenyl-, N-(4-methylphenyl)-, N-(2-methylphenyl)-, N-(4-ethylphenyl)-, N-(4-isopropylphenyl)-, N-(4-isobutylphenyl)-, N-(4-tert.-butylphenyl)-, N-(4-methoxyphenyl)-, N-(4-ethoxyphenyl)- and N-(4-butoxyphenyl)-carbamyl.

Amongst the above substituents A, cyano is preferred.

Specific examples of substituents X are chlorine, methyl, ethyl, methoxy, ethoxy and butoxy, n being 1 or 2. Preferably, X is hydrogen.

In addition to hydrogen, $R^1$ may be methyl, ethyl or 2-hydroxyethyl if $R^2$ is cyclohexyl, phenyl or substituted phenyl, eg. 4-methylphenyl, 4-ethylphenyl, 4-methoxyphenyl, 4-ethoxyphenyl, 4-butoxyphenyl or 4-isopropylphenyl. If $R^1$ is hydrogen, $R^2$ may also be $C_1$–$C_4$-alkyl, eg. methyl, ethyl, propyl, i-propyl, butyl, i-butyl or tert.-butyl.

Further specific examples of substituents $R^1$ and $R^2$ are:

(a) unsubstituted or substituted $C_1$–$C_6$-alkyl, eg. methyl, ethyl, n-propyl, n-butyl, pentyl, hexyl, 2-chloroethyl, 2-cyanoethyl, 2-hydroxyethyl, 2-methoxyethyl, 2-ethoxyethyl, 2-propoxyethyl, 2-butoxyethyl, 2-phenoxyethyl, 2-(ethanoyloxy)-ethyl, 2-(propanoyloxy)-ethyl, 2-(butanoyloxy)-ethyl, 2-(pentanoyloxy)-ethyl, 2-(methoxyethanoyloxy)-ethyl, 2-(ethoxyethanoyloxy)-ethyl, 2-(phenoxyethanoyloxy)-ethyl, 2-(carbomethoxy)-ethyl, 2-(carboethoxy)-ethyl, 2-(carbobutoxy)-ethyl and 2-(carbopropoxy)-ethyl;

(b) allyl and phenyl-$C_1$–$C_4$-alkyl, eg. benzyl, β-phenylethyl, β-phenylpropyl, α-phenylpropyl and phenylbutyl.

(c) Examples of saturated 5-membered and 6-membered heterocyclic structures

are N-pyrrolidinyl, N-piperidinyl, N-morpholinyl, N-piperazinyl and N'-$C_1$–$C_4$-alkylpiperazinyl, where the alkyl on the N' atom is methyl, ethyl, propyl or butyl.

Specific examples of substituents Y, in addition to those already mentioned explicitly, are:

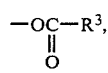 (a)

where $R^3$ is methyl, ethyl, propyl, butyl, hexyl, 1-ethylpentyl, heptyl, nonyl, undecyl, dodecyl, phenyl, 4-methylphenyl, 4-ethylphenyl, 4-methoxyphenyl or 4-ethoxyphenyl;

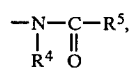 (b)

where $R^4$ is $C_1$–$C_4$-alkyl, eg. methyl, ethyl, or propyl, or is preferably hydrogen, and $R^5$ is hydrogen or (α) $R^5$ is $C_1$–$C_{12}$-alkyl, eg. methyl, ethyl, n-propyl, isopropyl, n-butyl, isobutyl, 2-methylpropyl, tert.-butyl, n-pentyl, 2,2-dimethylpropyl, 1-methylbutyl, 1-ethylpropyl, 1,1-dimethylpropyl, n-hexyl, 1,1-dimethylbutyl, 1,3-dimethylbutyl, heptyl, 1-ethyl-pentyl, 1-propylbutyl, 2,4-dimethylpentyl, octyl, nonyl, decyl, undecyl, 1,1-dimethylnonyl or dodecyl; or (β) $R^5$ is alkoxymethyl, phenoxymethyl or phenylthiomethyl, eg. methoxymethyl, ethoxymethyl, propoxymethyl or butoxymethyl; phenoxymethyl, 2-, 3- and 4-methylphenoxymethyl, 2-, 3- and 4-ethylphenoxymethyl, 4-tert.-butylphenoxymethyl, 4-isobutylphenoxymethyl, 4-tert.-butyl-2-methylphenoxymethyl, 2,3-dimethoxyphenoxymethyl, 2,4-dimethylphenoxymethyl, 2,5-dimethylphenoxymethyl, 3,5-dimethylphenoxymethyl, 3,4-dimethylphenoxymethyl, 2-, 3- and 4-chlorophenoxymethyl, 2-, 3- and 4-methoxyphenoxymethyl, 4-ethoxyphenoxymethyl, 2-methyl-4-chlorophenoxymethyl, 4-nitrophenoxymethyl, phenylthiomethyl, 4-methylphenylthiomethyl or 4-tert.-butylphenylthiomethyl; or (γ) $R^5$ is $C_3$–$C_7$-cycloalkyl, eg. cyclopropyl, cyclobutyl, cyclopentyl, cyclohexyl or cycloheptyl; or (δ) $R^5$ is phenyl, or phenyl substituted by alkyl, alkoxy or nitro, eg. 2-, 3- and 4-methylphenyl, 2-, 3- and 4-ethylphenyl, 2-, 3- and 4-n- or -i-propylphenyl, 2-, 3- and 4-n- or -i-butylphenyl, 4-dodecylphenyl, 4-methoxyphenyl, 4-ethoxyphenyl, 4-N- or 4-i-propoxyphenyl and 4-N- or 4-i-butoxyphenyl; or (ε) $R^5$ is a radical of the formula —$CH_2$—$PO(OR^6)_2$, where $R^6$ is methyl, ethyl, n- or i-propyl or n- or i-butyl; in addition $R^5$ may, as already mentioned, be trifluoromethyl, chloromethyl, benzyl, phenylethyl or $C_6H_5$—CH=CH—, or may be

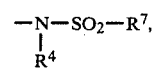 (c)

where $R^4$ is $C_1$–$C_4$-alkyl, eg. methyl, ethyl or propyl or, preferably, hydrogen, and $R^7$ is (α) $C_1$–$C_{12}$-alkyl, eg. methyl, ethyl, propyl, butyl, pentyl, hexyl, octyl, nonyl, decyl or dodecyl or (β) phenyl, phenyl substituted by $C_1$–$C_{12}$-alkyl, eg. 2-, 3- and 4-methylphenyl, 2-, 3- and 4-ethylphenyl, 2-, 3- and 4-isopropylphenyl, 2-, 3- and 4-isobutylphenyl, 4-pentylphenyl, 4-hexylphenyl, 4-octylphenyl, 4-nonylphenyl, 4-decylphenyl or 4-dodecylphenyl.

Further possible meanings of Y are $C_1$–$C_4$-alkylamino, eg. methylamino, ethylamino, propylamino and butylamino, if $R^1$ and $R^2$ are $C_1$–$C_4$-alkyl.

In addition, Y may be N,N-di-$C_1$–$C_4$-alkylamino, eg. dimethylamino, diethylamino, dipropylamino and dibutylamino, or N-pyrrolidinyl, N-piperidinyl, N-morpholinyl or N'-$C_1$–$C_4$-alkyl-piperazinyl, if

has the same meaning.

Preferably, Z is hydrogen.

Z may also be methoxy or ethoxy, if $R^1$ and $R^2$ are $C_1$–$C_4$-alkyl or allyl and Y is a group of the formula

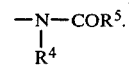

Amongst the compounds of the formula I, those of the formula (Ib)

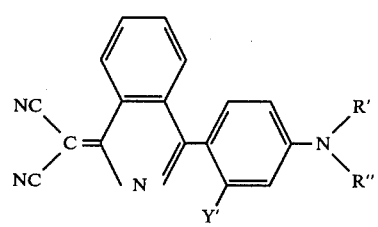 (Ib)

are preferred, for economic and tinctorial reasons.

In the formula (Ib),

Y' is hydrogen, hydroxyl,

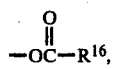

methyl, —NH—COR$^8$ or —NH—SO$_2$R$^9$, where R$^8$ is linear or branched C$_1$-C$_{12}$-alkyl, methoxymethyl, phenoxymethyl (where phenoxy is unsubstituted or substituted by methoxy or C$_1$-C$_4$-alkyl), phenylthiomethyl (where phenyl is unsubstituted or substituted by C$_1$-C$_4$-alkyl), benzyl, phenylethyl, phenyl, C$_1$-C$_{12}$-alkylphenyl, C$_6$H$_5$—CH=CH—, C$_3$-C$_7$-cycloalkyl, C$_1$-C$_4$-alkoxyphenyl, —CH$_2$—PO(OCH$_3$)$_2$, —CH$_2$—PO(OC$_2$H$_5$)$_2$, —CH$_2$—PO(OC$_3$H$_7$)$_2$ or —CH$_2$—PO(OC$_4$H$_9$)$_2$, R$^9$ is C$_1$-C$_{12}$-alkyl or is phenyl, which is unsubstituted or substituted by C$_1$-C$_{12}$-alkyl, and R$^{16}$ is C$_1$-C$_6$-alkyl or phenyl, and R' and R" are C$_1$-C$_4$-alkyl, 2-hydroxyethyl, C$_1$-C$_4$-alkoxyethyl, 2-phenoxyethyl, 2-chloroethyl, 2-cyanoethyl, 2-(carbomethoxy)-ethyl, 2-(carboethoxy)-ethyl, 2-(propanoyloxy)-ethyl, 2-(ethanoyloxy)-ethyl, allyl or benzyl, the substituents R' and R" being identical or different, or R' is hydrogen or methyl and R" is phenyl which is unsubstituted or substituted by methyl, ethyl, methoxy, or ethoxy, or is cyclohexyl, or

is N-pyrrolidinyl, N-piperidinyl or N-morpholinyl.

Particularly preferred compounds are those of the formula (Ib), where the group

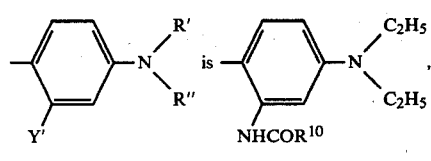

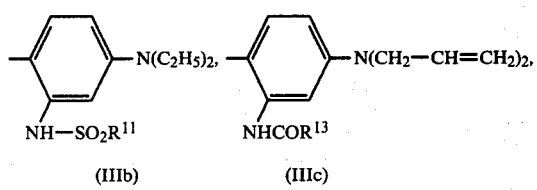

where

R$^{10}$ is linear or branched C$_1$-C$_{12}$-alkyl, methoxymethyl, phenoxymethyl (where phenoxy is unsubstituted or substituted by methoxy or C$_1$-C$_4$-alkyl), C$_3$-C$_7$-cycloalkyl, phenyl (which is unsubstituted or substituted by C$_1$-C$_4$-alkoxy or C$_1$-C$_4$-alkyl), benzyl, phenylethyl or C$_6$H$_5$—CH=CH—, R$^{11}$ is C$_1$-C$_{12}$-alkyl, phenyl or C$_1$-C$_{12}$-alkylphenyl, R$^{12}$ is hydrogen, methyl, ethyl, methoxy or ethoxy and R$^{13}$ is C$_1$-C$_6$-alkyl.

The dyes of the formula (I) or (Ib) may be employed as individual compounds or as mixtures of different dyes of the said formulae, or as mixtures with other dyes, for example, in the case of disperse dyes, as mixtures with other disperse dyes.

Amongst the above dyes, those of the formula (Ib), where is a radical of the formula and where R$^{18}$ is C$_1$-C$_{12}$-alkyl or phenoxymethyl and R$^{19}$ is methyl or ethyl, or mixtures of these dyes, are very particularly preferred for dyeing polyester fibers. These dyes give particularly deeply colored dyeings.

Amongst the last-mentioned dyes, those containing the radical of the formula (IIIf), where R$^{18}$ is methyl or ethyl, and mixtures of such dyes, are in turn preferred, since they exhibit extremely high tinctorial strength when used on polyesters.

Furthermore, amongst the dyes of the formula (Ib), those where R' and R" are ethyl and Y' is

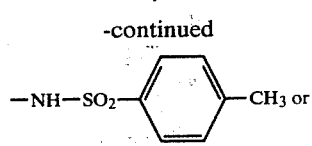

or

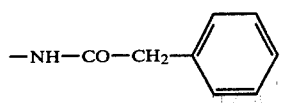

are very particularly preferred. These dyes exhibit a high tinctorial strength when used for the mass coloring of polystyrene.

The novel dyes of the formula (I) are obtained by reacting an isoindoline derivative of the formula

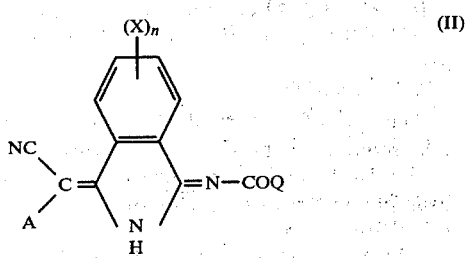

which may also be in one of its tautomeric forms, with an aromatic amine of the formula

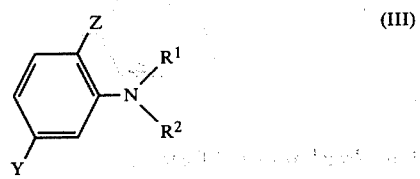

in an organic liquid in the presence of a catalytic amount of an acid. In the formulae (II) and (III), A, X, n, Y, Z, $R^1$ and $R^2$ have the meanings given above and Q is linear or branched $C_1$–$C_{12}$-alkyl or is phenyl which is unsubstituted or substituted by methyl, nitro or chlorine.

The compounds of the formula (II), required as starting materials, are prepared from 1,3-diiminoisoindolines, or from their tautomeric forms, by the following method:

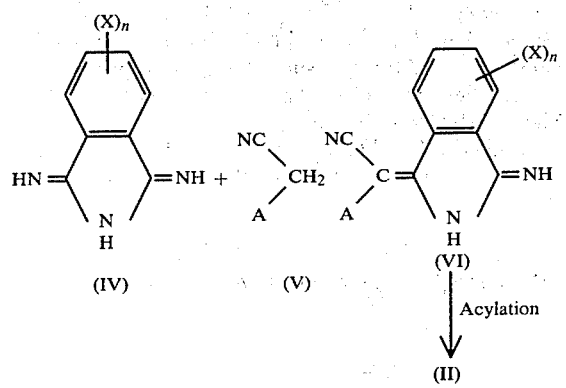

The condensation of IV, or of its tautomeric forms, with the methylene-active compound (V) is carried out in a conventional manner. Such reactions of one NH group of (IV) with (V) are described, for example, in German Laid-Open Application DOS No. 1,670,748. The acylation of the mono-reaction product (VI) is carried out in a conventional manner with the corresponding carboxylic acid anhydrides or carboxylic acid chlorides.

The reaction of (VI) with a carboxylic acid anhydride is advantageously carried out in an excess of the reagent, at from 80° to 150° C., preferably from 110° to 130° C. The acylation with a carboxylic acid chloride, eg. benzoyl chloride, is advantageously carried out in an inert organic solvent, eg. o-dichlorobenzene, chlorobenzene, nitrobenzene or naphthalene, in the presence of an acid-binding agent, eg. a tertiary amine.

Suitable acylating agents are acid chlorides or acid anhydrides of $C_2$–$C_{13}$-alkanoic acids, or of chloroacetic acid, benzoic acid, methylbenzoic acid, chlorobenzoic acid or nitrobenzoic acid.

For economic reasons, preferred acylating agents are those derived from acetic acid, propionic acid, butyric acid and benzoic acid.

Examples of suitable diimino-isoindolines of the formula (IV), which may also be in the form of the tautomeric amino-iminoisoindolenines, are 1,3-diiminoisoindoline, 1,3-diimino-5-methylisoindoline, 1,3-diimino-5-methoxyisoindoline, 1,3-diimino-5-ethoxyisoindoline, 1,3-diimino-5-butoxyisoindoline, 1,3-diimino-5-chloroisoindoline and 1,3-diimino-4,5-dichloro-indoline.

Examples of methylene-active compounds of the formula (V) are malodinitrile, $C_1$–$C_4$-alkyl cyanoacetates, eg. methyl, ethyl, n-propyl, isopropyl, n-butyl and i-butyl cyanoacetate; cyanoacetamide, cyanoacetic acid N-$C_1$–$C_4$-alkylamides and cyanoacetic acid N-($C_1$–$C_4$-alkoxy-$C_1$–$C_4$-alkyl)-amides, eg. N-methyl-, N-ethyl-, N-propyl-, N-butyl-, N-(3-methoxypropyl)-, N-(3-ethoxypropyl)- and N-(3-butoxypropyl)-cyanoacetamide; cyanoacetic acid N-phenylamides where phenyl is unsubstituted or substituted by $C_1$–$C_4$-alkoxy or $C_1$–$C_4$-alkyl, eg. N-phenyl-, N-(4-methylphenyl)-, N-(4-ethylphenyl)-, N-(4-methoxyphenyl)- or N-(4-ethoxyphenyl)-cyanoacetamide; cyanoacetone, ω-cyanoacetophenone, 4-nitrophenyl-acetonitrile and 4-cyanophenyl-acetonitrile.

Suitable starting components of the formula (III) are those which correspond to the relevant group in formula (I), and where Y, Z, $R^1$ and $R^2$ have the meanings given for these substituents.

Preferred aromatic amines are those of the formula

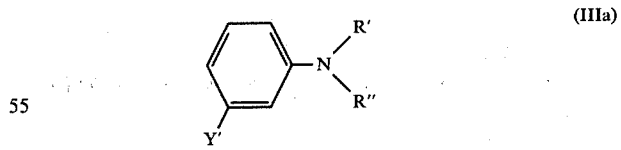

In formula IIIa, Y' is hydrogen, hydroxyl, methyl or a group of the formula —NH—CO—$R^8$, —NH—$SO_2$—$R^9$ or

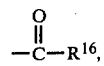

where $R^8$ is linear or branched $C_1$–$C_{12}$-alkyl, methoxymethyl, phenoxymethyl (where phenoxy is unsubstituted or substituted by methoxy or $C_1$–$C_4$-alkyl), phenylthiomethyl (where phenyl is unsubstituted or substituted by $C_1$-$C_4$-alkyl), benzyl, phenylethyl, phenyl, $C_1$-$C_{12}$-alkylphenyl, $C_6H_5$—CH=CH—, $C_3$-$C_7$-cycloalkyl, $C_1$-$C_4$-alkoxyphenyl, —$CH_2PO(OCH_3)_2$, —$CH_2PO(OC_2H_5)_3$, —$CH_2PO(OC_3H_7)_2$ or —$CH_2PO(OC_4H_9)_2$, $R^9$ is $C_1$-$C_{12}$-alkyl, phenyl or $C_1$-$C_{12}$-alkylphenyl, $R^{16}$ is $C_1$-$C_{16}$-alkyl or phenyl and R' and R", which may be identical or different, are $C_1$-$C_4$-alkyl, 2-hydroxyethyl, $C_1$-$C_4$-alkoxyethyl, 2-phenoxyethyl, 2-chloroethyl, 2-cyanoethyl, 2-(carbomethoxy)-ethyl, 2-(carboethoxy)-ethyl, 2-(propanoyloxy)-ethyl, 2-(ethanoyloxy)-ethyl, allyl or benzyl, and R' may also be hydrogen or methyl if R" is phenyl which is unsubstituted or substituted by methyl, ethyl, methoxy or ethoxy, or is cyclohexyl, and

may also be N-pyrrolidinyl, N-piperidinyl or N-morpholinyl.

To prepare a dye (I), the isoindoline derivative of the formula (II) is reacted (condensed) with at least the stoichiometric amount of the aromatic amine (III) at from 90° to 150° C., preferably from 110° to 130° C.

The condensation is carried out in an organic solvent, such as acetic anhydride, propionic anhydride, butyric anhydride, isobutyric anhydride, benzoic anhydride, an aromatic hydrocarbon, eg. benzene, toluene, xylene, mesitylene, chlorobenzene, dichlorobenzene, trichlorobenzene, nitrobenzene or naphthalene, tetrahydrothiophene S-dioxide, dimethylformamide, dimethylacetamide, N-methylpyrrolidone or a mixture of these.

If the reaction is carried out in a carboxylic acid anhydride, an acylation or trans-acylation reaction may take place on the component of the formula (III) and, if the reaction is carried out under appropriate conditions, this may for example be utilized in order to prepare dye mixtures.

Preferred catalytic acids are, in particular, mineral acids, aromatic and aliphatic sulfonic acids, and strongly acidic carboxylic acids, eg. concentrated sulfuric acid, phosphoric acid, hydrogen chloride, chloroacetic acid, dichloroacetic acid, trichloroacetic acid, trifluoroacetic acid, trifluoromethanesulfonic acid, benzenesulfonic acid, toluenesulfonic acid and methanesulfonic acid.

When synthesizing (I), it is not necessary to isolate the acylated monocondensation product (II). It is equally possible to react the non-acylated monocondensation product (VI) direct with the amine (III) in an acylating agent, eg. acetic anhydride or propionic anhydride, in the presence of catalytic amounts of an acid, to give (I).

An alternative procedure is first to react (VI) with the carboxylic acid anhydride and then to add the amine (III) and the catalytic amount of acid to the reaction mixture. The reaction to give the dye (I) takes place on subsequent heating.

The dyes may be isolated in a conventional manner by filtering the reaction mixture and washing the filter residue with an easily removable organic liquid which does not dissolve the dye, eg. methanol, ethanol or isopropanol.

The Examples which follow illustrate the invention. Parts and percentages are by weight. Parts by volume bear the same relation to parts as that of the liter to the kilogram.

In the Examples, the following coding of compounds by means of Roman numerals is used:

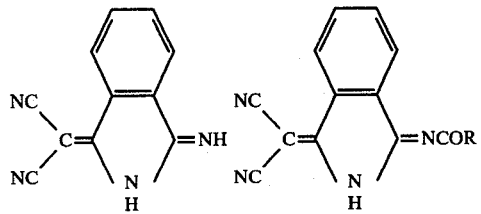

(VII) (VIII)

(a) R = —$CH_3$ VIII
(b) R = —$C_2H_5$

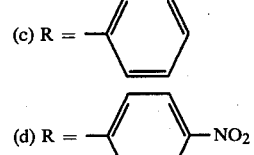(c) R =

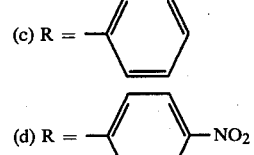(d) R = —NO$_2$

EXAMPLE 1

50 parts of compound VII in 250 parts by volume of acetic anhydride are stirred for 45 minutes at 120° C. After filtering off the product, washing it with methanol and drying it, 55 parts of compound (VIIIa), of melting point 226°–228° C., are obtained.

EXAMPLE 2

87 parts of compound VII in 250 parts by volume of propionic anhydride are heated for 30 minutes at 120°–130° C. After the mixture has cooled, the product is filtered off, washed with methanol and dried. 94.6 parts of compound (VIIb), of melting point 208°–210° C., are obtained.

EXAMPLE 3

A mixture of 87 parts of compound VII and 300 parts of benzoic anhydride is stirred for one hour at 120°–125° C. 500 parts by volume of methanol are then added at about 80° C., the mixture is allowed to cool and the precipitate is filtered off, washed with methanol, and dried. 103 parts of compound (VIIc), of melting point 226°–228° C., are obtained.

EXAMPLE 4

9.68 parts of benzoyl chloride are added to a mixture of 9.7 parts of compound VII, 150 parts by volume of toluene and 50 parts by volume of dry pyridine, and the mixture is boiled for 1.5 hours. Insoluble material is filtered off hot and the precipitate which crystallizes out from the filtrate is filtered off, washed with methanol and dried. Yield of compound (VII c): 6.9 parts, of melting point 225°–227° C.

EXAMPLE 5

11.3 parts of 4-nitrobenzoyl chloride are added to a mixture of 9.7 parts of compound VII, 100 parts by volume of toluene, 50 parts by volume of dimethylacetamide, and 50 parts by volume of dry pyridine, and the batch is refluxed for 3.5 hours. A further 11.3 parts of the acid chloride are then added and the mixture is boiled for 2 hours. 200 parts by volume of methanol are added cautiously and after stirring the mixture for one hour the product is filtered off, washed with methanol and dried. 11.7 parts of compound (VIII d), of melting point 254°–256° C., are obtained.

EXAMPLE 6

9.7 parts of compound VII and 6.2 parts of N,N-dimethylaniline in 150 parts by volume of acetic anhydride plus a few drops of concentrated sulfuric acid are heated for 1.5 hours at 120° C. After the mixture has cooled, the product is filtered off, washed with acetic anhydride and methanol and dried. 7.7 parts of a dye $CH_3$ are obtained; the product dyes polyesters in reddish blue hues.

EXAMPLE 7

9.65 parts of compound VII in 100 parts by volume of propionic anhydride are heated for 30 minutes at 120° C. 7.97 parts of N,N-diethylaniline and two drops of concentrated sulfuric acid are then added and the mixture is stirred for 3 hours at 120° C. After it has cooled, the product is filtered off, washed with methanol and with about 1,000 parts by volume of warm water, and dried. Yield: 7.3 parts of a dye of the formula (Ib), where Y' is H and R' and R" are each $C_2H_5$; the product dyes polyesters in reddish blue hues.

EXAMPLE 8

(a) 9.7 parts of compound VII and 12.5 parts of 3-diethylaminoacetanilide in 70 parts by volume of acetic anhydride plus a few drops of concentrated sulfuric acid are heated for 2.5 hours at 120°–130° C. The mixture is concentrated under reduced pressure and the precipitate obtained after cooling is filtered off and washed repeatedly with acetic anhydride and with a small amount of methanol. After drying the product, 4.1 parts of a dye of the formula (Ib), where Y' is $NHCOCH_3$ and R' and R" are each $C_2H_5$ are obtained; the product dyes polyesters in blue hues.

(b) 6.3 parts of compound (VIIIb), 6.3 parts of 3-diethylaminoacetanilide, 40 parts by volume of o-dichlorobenzene and two drops of concentrated sulfuric acid are stirred for 45 minutes at 120° C. After filtering off the product, washing it with methanol and drying it, 1.6 parts of a dye of the formula (Ib), where Y' is $NHCOCH_3$ and R' and R" are each $C_2H_5$, are obtained.

(c) 7.45 parts of compound (VIII c) and 6.3 parts of 3-diethylaminoacetanilide (83% pure) in 20 parts by volume of tetrahydrothiophene dioxide and three drops of concentrated sulfuric acid are heated at 120°–130° C. until the starting material is no longer detectable in a thin layer chromatogram. On isolating the product by the method described in Example 8 (b), 3.33 parts of a dye of the formula (Ib), where Y' is $NHCOCH_3$ and R' and R" are each $C_2H_5$, are obtained.

EXAMPLE 9

(a) 5 parts of compound (VIIIb) and 4.8 parts of propionic acid 3-diethylaminoanilide in 20 parts by volume of toluene and two drops of concentrated sulfuric acid are refluxed for 2 hours. After cooling the mixture, filtering off the product, washing it with methanol and warm water and drying it, 4.9 parts of a dye of the formula (Ib), where Y' is $NHCOC_2H_5$ and R' and R" are each $C_2H_5$, are obtained; the product dyes polyesters in blue hues.

(b) 7.5 parts of compound (VIIIb) and 6.7 parts of propionic acid 3-diethylaminoanilide in 30 parts by volume of mesitylene and two drops of concentrated sulfuric acid are heated for 2.5 hours at 120° C. On working up the mixture by the method described in Example 9 (a), 6.9 parts of a dye of the formula (Ib), where Y' is $NHCOC_2H_5$ and R' and R" are each $C_2H_5$, are isolated.

(c) 20 parts by volume of propionic anhydride are slowly added dropwise to 5.8 parts of 3-diethylaminoaniline. After stirring the mixture for a further hour at 50° C., 6.25 parts of compound (VIIIb) and a pinch of chloroacetic acid are added. The mixture is kept at 120°–130° C. for 30 minutes and, when it has cooled, is worked up by the method described in Example 9 (a). 6.8 parts of a dye of the formula (Ib), where Y' is $NHCOC_2H_5$ and R' and R" are each $C_2H_5$, are obtained.

If the procedure described above is followed but in place of chloroacetic acid a few drops of trifluoroacetic acid or of o-phosphoric acid are used, 6.7 parts and 8 parts of the same dye are respectively obtained.

(d) A mixture of 3.43 parts of compound (VIIId), 2.64 parts of propionic acid 3-diethylaminoanilide, 10 parts by volume of xylene, 10 parts by volume of dimethylacetamide and 1 drop of concentrated sulfuric acid is kept at 125° C. for 1.5 hours. The mixture is worked up by the method described in Example 9 (a). Yield: 0.9 part of a dye of the formula Ib), where Y' is $NHCOC_2H_5$ and R' and R" are each $C_2H_5$.

EXAMPLE 10

25 parts by volume of propionic anhydride are slowly added dropwise to 8.2 parts of 3-diethylaminoaniline, the mixture is stirred for 1 hour at 50° C., and 12.5 parts of 3-diethylaminoacetanilide, 19.2 parts of compound VII and a few drops of concentrated sulfuric acid are then added to the reaction solution. This mixture is stirred for 1.5 hours at 130° C. The crystals which precipitate on cooling are isolated, washed with acetic anhydride, methanol and warm water, and dried. 8.2 parts of dye are obtained. The dye is a mixture of 2 components of the formula (Ib), where R' and R" are each $C_2H_5$, and Y' is $NHCOCH_3$ and $NHCOC_2H_5$ respectively. The dye mixture gives blue hues on polyesters.

EXAMPLE 11

10 parts of 3-diethylaminoaniline in 25 parts by volume of formic acid are refluxed for 45 minutes. The residue left on concentrating the mixture is mixed with 9.5 parts of compound VII, 40 parts by volume of propionic anhydride and three drops of concentrated sulfuric acid. After having been stirred for two hours at 120° C., the mixture is allowed to cool and the precipitate is filtered off and washed with ethanol. The filter residue is then thoroughly stirred with water, filtered off, washed with water and dried. 2.7 parts of dye are obtained. The dye is a mixture of 2 components of the formula (Ib), where Y' is —NH—CHO and —NH—$COC_2H_5$ respectively and R' and R" are each $C_2H_5$. The mixture dyes polyesters in blue hues.

EXAMPLE 12

A mixture of 13.3 parts of compound VII, 18.7 parts of butyric acid 3'-diethylaminoanilide, 70 parts by volume of propionic anhydride and a few drops of concentrated sulfuric acid is heated for 30 minutes at 120° C. When it has cooled, the mixture is filtered and the residue is washed with methanol and warm water, and dried. 14.4 parts of a dye of the formula (Ib), where Y' is —NHCOCH$_2$CH$_2$CH$_3$ and R' and R" are each —C$_2$H$_5$, are obtained; the product dyes polyesters in blue hues.

EXAMPLE 13

If 20.9 parts of caproic acid 3-diethylaminoanilide are used and Example 12 is followed, 18.7 parts of a dye mixture, which gives blue hues on polyesters, are obtained. The mixture contains 2 dyes of the formula (Ib), where R' and R" are each —C$_2$H$_5$ and Y' is —NHCO(CH$_2$)$_4$CH$_3$ and —NHCOC$_2$H$_5$ respectively.

EXAMPLE 14

If 22 parts of enanthic acid 3-diethylaminoanilide are used and in other respects the procedure followed is as described in Example 12, 15.6 parts of a mixture of dyes of the formula (Ib), where Y' is —NHCO(CH$_2$)$_5$CH$_3$ and —NHCOC$_2$H$_5$ respectively, and R' and R" are each C$_2$H$_5$, are obtained; the product dyes polyesters in blue hues.

EXAMPLE 15

If 23.2 parts of caprylic acid 3-diethylaminoanilide are used and in other respects the procedure described in Example 12 is followed, 18.1 parts of a mixture of two dyes of the formula (Ib), where Y' is —NHCO(CH$_2$)$_6$CH$_3$ and —NHCOC$_2$H$_5$ respectively and R' and R" are each —C$_2$H$_5$, are obtained; the product dyes polyesters in blue hues.

EXAMPLE 16

A mixture of 11.4 parts of compound VII, 14.9 parts of valeric acid 3-diethylaminoanilide, 30 parts by volume of propionic anhydride and two drops of concentrated sulfuric acid is immersed in an oil bath at 120° C. After 15 minutes, the mixture is allowed to cool and is worked up as described in Example 12. 12.2 parts of the dye of the formula (Ib), where Y' is —NHCO(CH$_2$)$_3$CH$_3$ and R' and R" are each —C$_2$H$_5$, are obtained; the product dyes polyesters in blue hues.

EXAMPLE 17

If 15.2 parts of pelargonic acid 3-diethylaminoanilide and 9.5 parts of compound VII are used, and in other respects the procedure followed is as described in Example 16, 11.2 parts of a dye of the formula (Ib), where Y' is —NHCO(CH$_2$)$_7$CH$_3$ and R' and R" are each —C$_2$H$_5$, are obtained; the product dyes polyesters in blue hues.

EXAMPLE 18

If 15.9 parts of capric acid 3-diethylaminoanilide and 9.5 parts of compound VII are used, and in other respects the procedure followed is as described in Example 16, 11.1 parts of a dye of the formula (Ib), where Y' is —NHCO(CH$_2$)$_8$CH$_3$ and R' and R" are each C$_2$H$_5$ are obtained; the product dyes polyesters in blue hues.

EXAMPLE 19

If 17.1 parts of lauric acid 3-diethylaminoanilide and 9.5 parts of compound VII are used, and in other respects the procedure followed is as described in Example 16, 9.8 parts of a dye of the formula (Ib), where Y' is —NHCO(CH$_2$)$_{10}$CH$_3$ and R' and R" are each —C$_2$H$_5$, are obtained; the product dyes polyesters in blue hues.

The dyes prepared according to Examples 16 to 19 contain only very small amounts of the dye of the formula (Ib) where Y' is —NHCOC$_2$H$_5$ and R' and R" are each —C$_2$H$_5$.

EXAMPLE 20

If 11.8 parts of methoxyacetic acid 3-diethylaminoanilide and 9.5 parts of compound VII are used and in other respects the procedure of Example 16 is followed, 8 parts of a mixture of dyes of the formula (Ib), where Y' is —NHCOCH$_2$OCH$_3$ and —NHCOC$_2$H$_5$ respectively and R' and R" are each —C$_2$H$_5$, are obtained. The mixture dyes polyesters in blue hues.

EXAMPLE 21

9.7 parts of compound VII, 12.5 parts of pivalic acid 3-diethylaminoanilide, 40 parts by volume of propionic anhydride and about one part by volume of concentrated sulfuric acid are heated for 1.5 hours at 120°–130° C. The solution is partially concentrated under reduced pressure and the resulting precipitate is filtered off and washed with acetic anhydride, methanol and water. It is then digested with about 20 parts of acetic anhydride, filtered off and washed with methanol and warm water. 6.55 parts of a dye of the formula (Ib), where Y' is —NHCOC(CH$_3$)$_3$ and R' and R" are each —C$_2$H$_5$, are obtained; the product dyes polyesters in blue hues.

EXAMPLE 22

7.76 parts of compound VII and 17.7 parts of 2-ethylhexanoic acid 3'-diethylaminoanilide in 25 parts by volume of propionic anhydride plus a few drops of concentrated sulfuric acid are heated for 1.5 hours at 130° C. The mixture is concentrated under reduced pressure and poured into water. After standing for some time, the precipitate is filtered off. The filter residue is washed with methanol, acetic acid and warm water and dried. 2.6 parts of a dye of the formula (Ib), where Y' is

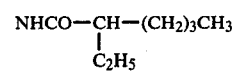

and R' and R" are each C$_2$H$_5$, are obtained; the product dyes polyesters in blue hues.

EXAMPLE 23

A mixture of 20.9 parts of 3,3-dimethyl-propionic acid 3'-diethylaminoanilide, 13.3 parts of compound VII, 70 parts by volume of propionic anhydride and a few drops of concentrated sulfuric acid is heated for 30 minutes at 120° C. After working up by the method described in Example 12, 15.8 parts of a mixture, containing two dyes of the formula (Ib), where Y' is —NHCOCH$_2$C(CH$_3$)$_3$ and —NHCOC$_2$H$_5$ respectively and R' and R" are each —C$_2$H$_5$, are obtained. The mixture dyes polyesters in blue hues.

EXAMPLE 24

Following the procedure of Example 16, using 9.5 parts of compound VII and 14.1 parts of phenylacetic acid 3'-diethylaminoanilide, 9.9 parts of a dye of the formula (Ib), where Y' is —NHCOCH$_2$C$_6$H$_5$ and R' and R" are each —C$_2$H$_5$, are obtained; the product dyes polyesters in blue hues.

EXAMPLE 25

Following the procedure of Example 16, using 9.5 parts of compound VII and 14.9 parts of 4-methoxybenzoic acid 3'-diethylaminoanilide, 13.1 parts of a dye of the formula (Ib), where Y' is —NHCO—C$_6$H$_4$—4—OCH$_3$ and R' and R" are each —C$_2$H$_5$, are obtained; the product dyes polyesters in blue hues.

EXAMPLE 26

A mixture of 7.8 parts of trifluoroacetic acid 3-diethylaminoanilide, 8.94 parts of compound (VIII c), 30 parts by volume of tetrahydrothiophene dioxide and two drops of concentrated sulfuric acid is heated for 30 minutes at 120° C. The precipitate which separates out after the mixture has stood for several days is filtered off, washed and dried. 1.2 parts of a dye of the formula (Ib), where Y' is —NHCOCF$_3$ and R' and R" are each —C$_2$H$_5$, are obtained; the product dyes polyesters in reddish blue hues.

EXAMPLE 27

9.7 parts of compound VII and 17.8 parts of phenoxyacetic acid 3-diethylaminoanilide in 50 parts by volume of acetic anhydride plus a few drops of concentrated sulfuric acid are heated for 75 minutes at 120°–130° C. After the mixture has cooled the product is filtered off, washed with acetic anhydride and methanol, and dried. 8 parts of a dye of the formula (Ib), where Y' is —NHCOCH$_2$OC$_6$H$_5$ and R' and R" are each —C$_2$H$_5$, are obtained; the product dyes polyesters in blue hues.

EXAMPLE 28

A mixture of 34.5 parts of 4-chloro-2-methylphenoxyacetic acid 3'-diethylaminoanilide, 19 parts of compound VII, 90 parts by volume of propionic anhydride and a few drops of concentrated sulfuric acid is heated for 1.5 hours at 120° C. After working up as described in Example 12, 21.7 parts of a dye of the formula (Ib), where Y' is

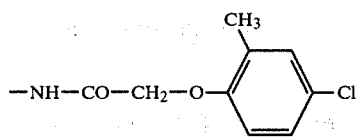

and R' and R" are each —C$_2$H$_5$, are obtained; the product dyes polyesters in blue hues.

EXAMPLE 29

A mixture of 9 parts of compound (VIIIb), an excess of crude phenylthioacetic acid 3-diethylaminoanilide (obtained from chloroacetic acid 3'-diethylaminoanilide and thiophenol), 25 parts by volume of xylene and 2 drops of concentrated sulfuric acid is heated for 1 hour at 110°–120° C. After adding 20 parts by volume of dimethylacetamide, the mixture is kept at 120° C. for 45 minutes and is then cooled. The precipitate formed is filtered off, washed with methanol, stirred with about 500 parts by volume of water, again filtered off, washed with warm water and dried. 6.24 parts of a dye which gives blue hues on polyesters are obtained. The dye essentially consists of a compound of the formula (Ib), where Y' is

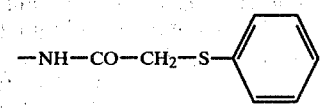

and R' and R" are each —C$_2$H$_5$.

EXAMPLE 30

A mixture of 6.25 parts of compound (VIIIb), an excess of crude

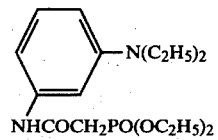

(prepared from chloroacetic acid 3-diethylaminoanilide and triethyl phosphite), 20 parts by volume of xylene and a few drops of concentrated sulfuric acid is refluxed for 1.5 hours. After it has cooled, the reaction mixture is poured into dilute sodium carbonate solution, the batch is left to stand overnight and the product is filtered off, washed with water, stirred thoroughly with hot water, again filtered off and dried. 7.2 parts of a dye which gives blue hues on polyesters are obtained. The dye essentially consists of a compound of the formula (Ib), where Y' is —NHCO—CH$_2$—PO(OC$_2$H$_5$)$_2$ and R' and R" are each —C$_2$H$_5$.

EXAMPLE 31

14.5 parts of methanesulfonic acid 3-diethylaminoanilide, 10.4 parts of compound VII, 50 parts by volume of propionic anhydride and three drops of concentrated sulfuric acid are heated for 1.5 hours at 120° C. On working up as described in Example 12, 9.8 parts of a dye of the formula (Ib), where Y' is —NHSO$_2$CH$_3$ and R' and R" are each —C$_2$H$_5$, are obtained; the product dyes polyesters in reddish blue hues. The dye contains small proportions of the dye where Y' is —NHCOC$_2$H$_5$.

EXAMPLE 32

A mixture of 13.3 parts of compound VII, 50 parts by volume of propionic anhydride and three drops of concentrated sulfuric acid is rapidly heated to 120° C. At this temperature, 20.3 parts of propionic acid 3-diallylaminoanilide are added over 10 minutes, and the mixture is kept at 120°–130° C. for a further 30 minutes and then worked up. 14.3 parts of a dye which gives reddish blue hues on polyesters are obtained. The dye very largely consists of a compound of the formula (Ib), where Y' is —NH—COC$_2$H$_5$ and R' and R" are each —CH$_2$—CH=CH$_2$.

EXAMPLE 33

5 parts of compound (VIIIb) and 5.12 parts of 3-N,N-diethylamino-acetanilide in 20 parts by volume of acetic anhydride and 2 drops of concentrated sulfuric acid are refluxed for 1 hour. The precipitate which separates out after several days' standing is isolated as described in Example 12. 0.85 part of a dye which gives violet hues on polyesters is obtained. The dye consists of a mixture of the compounds of the formula (Ib) where Y' is —N-

H—CO—CH₃ and R' and R" are each either —C₂H₄—OH or —C₂H₄OCOCH₃.

EXAMPLE 34

19.4 parts of compound VII, 23 parts of N-methyl-4-ethoxydiphenylamine, 100 parts by volume of acetic anhydride and 1 part by volume of concentrated sulfuric acid are heated for 1 hour at 120° C. After the mixture has cooled, the product is filtered off, washed with methanol and dried. 19 parts of a dye which gives blue hues on polyesters are obtained. The dye essentially consists of a compound of the formula (Ib), where Y' is H, R' is —CH₃ and R" is

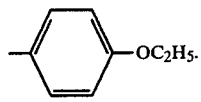

EXAMPLE 35

A mixture of 5.76 parts of compound (VIII c), 3.42 parts of N,N-diethyl-m-toluidine, 20 parts by volume of propionic anhydride and two drops of concentrated sulfuric acid is heated for one hour at 120° C. After adding a further part of N,N-diethyl-m-toluidine, the mixture is kept for 2 hours at the same temperature; after it has cooled, it is worked up as described in Example 12. 3.55 parts of a dye of the formula (Ib), where Y' is —CH₃ and R' and R" are each —C₂H₅, are obtained; the product dyes polyesters in reddish blue hues.

EXAMPLE 36

7.5 parts of compound (VIII c) and 6.1 parts of the compound of the formula

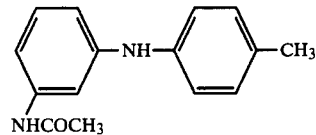

in 25 parts by volume of xylene plus two drops of concentrated sulfuric acid are heated for 2 hours at 120° C. After the mixture has cooled, the product is filtered off, washed with dimethylformamide and methanol, and dried. 3.7 parts of a dye of the formula (Ib), where Y' is —NHCOCH₃, R' is H and R" is —C₆H₄—4—CH₃, are obtained; the product dyes polyesters in blue hues.

EXAMPLE 37

13.3 parts of compound VII in 40 parts by volume of acetic anhydride, to which two drops of concentrated sulfuric acid have been added, are rapidly heated to 120° C. 18.8 parts of 3-diethylamino-4-methoxyacetanilide are introduced in portions, over 10 minutes, into the reaction mixture. The mixture is stirred for a further 2 hours at 120° C. and is then worked up in a conventional manner. 9 parts of a dye of the formula I, where A is —CN, Z is —OCH₃, Y is —NHCOCH₃ and R¹ and R² are each —C₂H₅, are obtained; the product dyes polyesters in greenish blue hues.

EXAMPLE 38

30 parts by volume of propionic anhydride are added slowly to 13.2 parts of 3-diethylaminoaniline; the solution is stirred for one hour at 50° C. and 20.8 parts of the compound

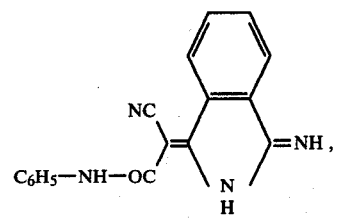

20 parts by volume of propionic anhydride and three drops of concentrated sulfuric acid are then added. After 4.5 hours at 120° C., the mixture is allowed to cool and is filtered, and the filtrate is poured into water. The precipitate, which crystallizes slowly, is filtered off and washed with warm water; it is then stirred thoroughly with 1% strength sodium hydroxide solution, filtered off, washed with water and methanol and dried. 31 parts of a dye which gives violet hues on polyesters are obtained. The dye essentially consists of compound of the formula I, where A is —CONH—C₆H₅, Y is —NHCOC₂H₅, Z is H and R¹ and R² are each C₂H₅.

EXAMPLE 39

9.9 parts of compound VII, 7 parts of 3-dimethylaminophenol, 200 parts by volume of acetic anhydride and about 1 part by volume of concentrated sulfuric acid are heated for 3 hours at 100°–120° C. The reaction mixture is then partially concentrated and cooled in an ice-bath, and the precipitate formed is filtered off, washed with a small amount of acetic anhydride and methanol, and dried. The yield of dye is 7 parts; the product dyes polyesters in violet hues. The dye has the formula (Ib), where Y' is OH and R' and R" are each —CH₃.

EXAMPLE 40

9.7 parts of compound VII, 10 parts of 3-morpholinophenol, 75 parts by volume of acetic anhydride and 0.5 part by volume of concentrated sulfuric acid are heated for 1.5 hours at 120°–130° C. After the mixture has cooled, it is worked up as described in Example 39, giving 5.65 parts of a mixture of 2 dyes of the formula (Ib), where Y' is —OH and —OCOCH₃ and

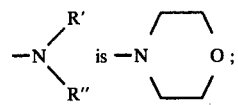

the product dyes polyesters in violet hues.

EXAMPLE 41

4.85 parts of compound VII and 20 parts by volume of propionic anhydride are heated for 30 minutes at 120° C. After adding 4.58 parts of 3-pyrrolidinophenol, 40 parts by volume of propionic anhydride and 2 drops of concentrated sulfuric acid, the mixture is heated for one hour at 120° C. After working up, 4.46 parts of a mixture of 2 dyes of the formula (Ib), where Y' is OH and —OCOC₂H₅ respectively and

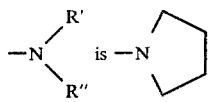

are obtained; the product dyes polyesters in violet hues.

EXAMPLE 42

6.2 parts of compound (VIIIb), 5.44 parts of N-ethyl-N-(2-chloroethyl)-aniline, 20 parts by volume of propionic anhydride and 2 drops of concentrated sulfuric acid are heated for 15 minutes at 120° C. 5 parts of a dye of the formula (Ib), where Y' is H, R' is —$C_2H_5$ and R" is —$CH_2CH_2Cl$, are obtained; the product dyes polyesters in reddish blue hues.

EXAMPLE 43

9.7 parts of compound VII, 14 parts of benzoic acid 3-diethylaminoanilide, 45 parts by volume of propionic anhydride and a few drops of concentrated sulfuric acid are heated for 1.5 hours at 130° C. After the mixture has cooled, the product is filtered off and washed successively with acetic acid, with methanol, with warm water, with a small amount of dimethylformamide and again with methanol and with water, and dried. 8.9 parts of a dye of the formula (Ib), where Y' is —$NHCOC_6H_5$ and R' and R" are each —$C_2H_5$, are obtained; the product dyes polystyrene in blue hues.

EXAMPLE 44

9.5 parts of compound VII, 14.2 parts of p-toluic acid 3-diethylaminoanilide, 35 parts by volume of propionic anhydride and a few drops of concentrated sulfuric acid are heated for 1.5 hours at 130° C. After filtering off the product, washing it with methanol and water and drying it, 10.1 parts of a dye of the formula (Ib), where Y' is

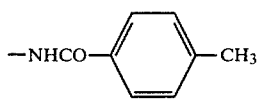

and R' and R" are each —$C_2H_5$, are obtained; the product dyes polystyrene in blue hues.

EXAMPLE 45

6.2 parts of compound (VIIIb) and 7.8 parts of 4-ethylbenzoic acid 3'-diethylaminoanilide in 20 parts by volume of propionic anhydride and two drops of concentrated sulfuric acid are heated for 30 minutes at 130° C. After working up as described in Example 44, 6.87 parts of a dye of the formula (Ib), where Y' is

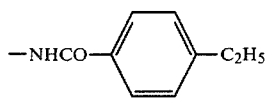

and R' and R" are each —$C_2H_5$, are obtained; the product dyes polystyrene in blue hues.

EXAMPLE 46

1.93 parts of compound (VIIIb) and 2.4 parts of 4-nitrobenzoic acid 3'-diethylaminoanilide, reacted similarly to Example 45, give 2 parts of a dye of the formula (Ib), where Y' is

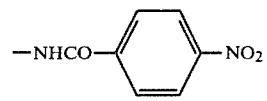

and R' and R" are each —$C_2H_5$; the product dyes polystyrene in blue hues.

EXAMPLE 47

9.7 parts of compound VII, 15 parts of cinnamic acid 3'-diethylaminoanilide, 38 parts by volume of propionic anhydride and a few drops of concentrated sulfuric acid are heated for 1 hour at 130° C. After working up, 10.1 parts of a dye of the formula (Ib), where Y' is —$NHCO-CH=CH-C_6H_5$ and R' and R" are each —$C_2H_5$, are obtained; the product dyes polystyrene in blue hues.

EXAMPLE 48

9.7 parts of compound VII, 16 parts of 4-toluenesulfonic acid 3'-diethylaminoanilide, 20 parts by volume of propionic anhydride and a few drops of concentrated sulfuric acid are heated for 1 hour at 130° C. After the mixture has cooled, 10 parts by volume of acetic acid are added and the precipitate is filtered off, washed with methanol, then with a small amount of dimethylformamide, and thereafter with methanol and with warm water. After drying, 9.75 parts of a dye of the formula (Ib), where Y' is

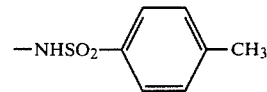

and R' and R" are each —$C_2H_5$, are obtained; the product dyes polystyrene in reddish blue hues.

EXAMPLE 49

6.25 parts of compound (VIIIb), 5.7 parts of N-ethyl-N-benzyl-aniline, 20 parts by volume of propionic anhydride and 2 drops of concentrated sulfuric acid are stirred for 1 hour at 120°–130° C. After working up, 7.75 parts of a dye of the formula (Ib), where Y' is —H, R' is —$C_2H_5$ and R" is —$CH_2C_6H_5$, are obtained; the product dyes polyesters in violet hues.

EXAMPLE 50

6.25 parts of compound (VIIIb) and 6.1 parts of N-ethyl-N-benzyl-3-methylaniline, reacted as described in Example 49, give 5.1 parts of a dye of the formula (Ib), where Y' is —$CH_3$, R' is —$C_2H_5$ and R" is —$CH_2C_6H_5$; the product dyes polyesters in violet hues.

EXAMPLE 51

5.76 parts of compound (VIII c), 3.9 parts of N,N-dimethyl-3-methyl-aniline, 20 parts by volume of propionic anhydride and 2 drops of concentrated sulfuric acid are heated for 2 hours at 120°–130° C. After working up, 4 parts of a dye of the formula (Ib), where Y' is —$CH_3$ and R' and R" are each —$CH_3$, are obtained; the product dyes polyesters in violet hues.

EXAMPLE 52

5.76 parts of compound (VIII c) and 4.4 parts of N,N-diethyl-3-methylaniline, reacted as described in Example 51, give 3.55 parts of a dye of the formula (Ib), where Y' is —CH$_3$ and R' and R" are each —C$_2$H$_5$, which dyes polyesters in violet hues.

EXAMPLE 53

A mixture of 9.5 parts of compound VII, 14.1 parts of phenylacetic acid 3'-diethylaminoanilide, 30 parts by volume of propionic anhydride and two drops of concentrated sulfuric acid is reacted as described in Example 16. 9.9 parts of a dye of the formula (Ib), where Y' is —NHCOCH$_2$C$_6$H$_5$ and R' and R" are each —C$_2$H$_5$, are obtained; the product dyes polystyrene in blue hues.

EXAMPLE 54

1.93 parts of compound (VIII c), 2.4 parts of 4-nitrobenzoic acid 3'-diethylaminoanilide and 1 drop of concentrated sulfuric acid are heated for 2 hours at 120°–130° C. After working up in a conventional manner, 2 parts of a dye of the formula (Ib), where Y' is

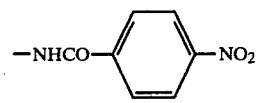

and R' and R" are each —C$_2$H$_5$, are obtained; the product dyes polystyrene in blue hues.

EXAMPLE 55

13.3 parts of compound VII, 50 parts by volume of propionic anhydride and 2 drops of concentrated sulfuric acid are heated at 120° C. 21.8 parts of cyclohexanecarboxylic acid 3-diethylaminoanilide are added in the course of 5 minutes and stirring is continued for 30 minutes at 120° C. After working up in a conventional manner, 18.3 parts of a dye of the formula (Ib), where Y' is

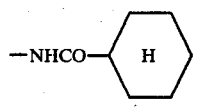

and R' and R" are each —C$_2$H$_5$, containing small proportions of the dye where Y' is —NHCOC$_2$H$_5$, are obtained. The mixture dyes polyesters in blue hues.

EXAMPLE 56

2.4 parts of the compound of the formula

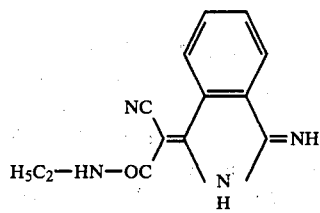

and 15 parts by volume of propionic anhydride are heated for 30 minutes at 110°–120° C. After adding 3 parts of phenoxyacetic acid 3'-diethylaminoanilide and 2 drops of concentrated sulfuric acid, the mixture is stirred for 1.5 hours at 120°–130° C. and is filtered after it has cooled. The residue is thoroughly washed with methanol. The combined filtrates are stirred into dilute sodium carbonate solution. After the mixture has stood overnight, the precipitate is filtered off, washed with warm water and dried. 2.6 parts of a dye of the formula I, where A is —CONHC$_2$H$_5$, Y is —NHCOCH$_2$OC$_6$H$_5$, R$^1$ and R$^2$ are each C$_2$H$_5$ and Z is H, are obtained; the product dyes polyesters in violet hues.

We claim:
1. A dye of the formula

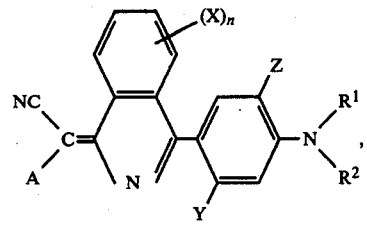

wherein

A is cyano, carbo-C$_1$-C$_4$-alkoxy, acetyl, benzoyl, 4-nitrophenyl, 4-cyanophenyl, carbamyl, N-C$_1$-C$_4$-alkylcarbamyl, where alkyl is unsubstituted or substituted by C$_1$-C$_4$-alkoxy, or N-phenylcarbamyl, where phenyl is unsubstituted or substituted by C$_1$-C$_4$-alkyl or C$_1$-C$_4$-alkoxy, X is hydrogen, chlorine, C$_1$-C$_4$-alkyl or C$_1$-C$_4$-alkoxy, and if n is 2 the substituents may be identical or different, n is 1 or 2, R$^1$ is hydrogen, methyl, ethyl or 2-hydroxyethyl and R$^2$ is phenyl which is unsubstituted or substituted by C$_1$-C$_4$-alkyl or C$_1$-C$_4$-alkoxy, or is cyclohexyl, or R$^1$ is hydrogen and R$^2$ is C$_1$-C$_4$-alkyl or R$^1$ and R$^2$ are C$_1$-C$_6$-alkyl; C$_1$-C$_4$-alkyl substituted by chlorine, cyano, hydroxyl, C$_1$-C$_4$-alkoxy, phenoxy, C$_2$-C$_5$-alkanoyloxy (which may or may not be substituted by C$_1$-C$_4$-alkoxy or phenoxy) or carbo-C$_1$-C$_4$-alkoxy; allyl; or phenyl-C$_1$-C$_4$-alkyl or

is a saturated heterocyclic five-membered or six-membered ring which may additionally contain an oxygen or a further nitrogen as a ring member, Y is hydrogen, hydroxyl, methyl or ethyl;

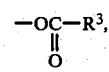

where R$^3$ is linear or branched C$_1$-C$_{12}$-alkyl or phenyl which is unsubstituted or substituted by C$_1$-C$_4$-alkyl or C$_1$-C$_4$-alkoxy;

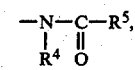

where $R^4$ is hydrogen or $C_1-C_4$-alkyl and $R^5$ is hydrogen, linear or branched $C_1-C_{12}$-alkyl, trifluoromethyl, chloromethyl, $C_1-C_4$-alkoxymethyl or phenoxymethyl (where phenoxy may or may not be substituted by one or two chlorine, methoxy, nitro or $C_1-C_4$-alkyl, and, in the case of two substituents, the substituents may be identical or different); phenylthiomethyl, where phenyl is unsubstituted or substituted by $C_1-C_4$-alkyl; benzyl; phenylethyl; $C_3-C_7$-cycloalkyl; phenyl which is unsubstituted or substituted by $C_1-C_{12}$-alkyl, $C_1-C_{12}$-alkoxy or nitro; $H_5C_6-CH=CH-$; $-CH_2-PO(OR^6)_2$, where $R^6$ is $C_1-C_4$-alkyl, or

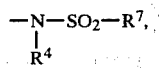

where $R^4$ has the above meanings and $R^7$ is $C_1-C_{12}$-alkyl, phenyl or $C_1-C_{12}$-alkylphenyl, or Y is $N-C_1-C_4$-alkylamino, when $R^1$ and $R^2$ are $C_1-C_4$-alkyl or Y is $N,N$-di-$C_1-C_4$-alkylamino, N-pyrrolidinyl, N-piperidinyl or N-morpholinyl when

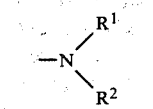

is $N,N$-di-$C_1-C_4$-alkylamino, N-pyrrolidinyl, N-piperidinyl or N-morpholinyl, and Z is hydrogen or, when $R^1$ and $R^2$ are $C_1-C_4$-alkyl or allyl and Y is

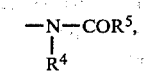

Z is hydrogen, methoxy or ethoxy.

2. The dye as claimed in claim 1, wherein A is cyano, N-phenylcarbamyl or N-ethylcarbamyl and X is hydrogen.

3. The dye as claimed in claim 1 or 2, wherein Y is hydrogen, hydroxyl,

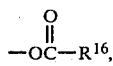

methyl, $-NH-COR^8$ or $-NH-SO_2R^9$, where $R^8$ is linear or branched $C_1-C_{12}$-alkyl, methoxymethyl, phenoxymethyl (where phenoxy is unsubstituted or substituted by methoxy or $C_1-C_4$-alkyl), phenylthiomethyl (where phenyl is unsubstituted or substituted by $C_1-C_4$-alkyl), benzyl, phenylethyl, phenyl, $C_1-C_{12}$-alkylphenyl, $C_6H_5-CH=CH-$, $C_3-C_7$-cycloalkyl, $C_1-C_4$-alkoxyphenyl, $-CH_2-PO(OCH_3)_2$, $-CH_2-PO(OC_2H_5)_2$, $-CH_2-PO(OC_3H_7)_2$ or $-CH_2-PO(OC_4H_9)_2$, $R^9$ is $C_1-C_{12}$-alkyl or is phenyl, which is unsubstituted or substituted by $C_1-C_{12}$-alkyl, and $R^{16}$ is $C_1-C_6$-alkyl or phenyl.

4. A dye as claimed in claim 1 or 2, wherein $R^1$ and $R^2$ are $C_1-C_4$-alkyl, 2-hydroxyethyl, $C_1-C_4$-alkoxyethyl, 2-phenoxyethyl, 2-chloroethyl, 2-cyanoethyl, 2-(carbomethoxy)-ethyl, 2-(carboethoxy)-ethyl, 2-(propanoyloxy)-ethyl, 2-(ethanoyloxy)-ethyl, allyl or benzyl, the substituents $R^1$ and $R^2$ being identical or different, or $R^1$ is hydrogen or methyl and $R^2$ is phenyl which is unsubstituted or substituted by methyl, ethyl, methoxy or ethoxy, or is cyclohexyl, or

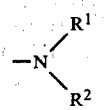

is pyrrolidinyl, piperidinyl or morpholinyl.

5. A dye of the formula

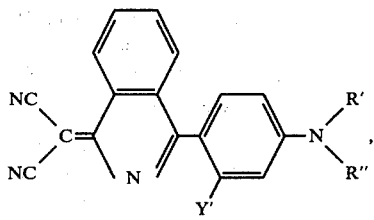

where

Y' is hydrogen, hydroxyl, methyl,

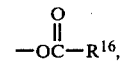

$-NHCOR^8$ or $-NHSO_2-R^9$, $R^{16}$ is $C_1-C_6$-alkyl or phenyl, $R^8$ is linear or branched $C_1-C_{12}$-alkyl, methoxymethyl, phenoxymethyl (where phenoxy is unsubstituted or substituted by methoxy or $C_1-C_4$-alkyl), phenylthiomethyl (where phenyl is unsubstituted or substituted by $C_1-C_4$-alkyl), benzyl, phenylethyl, phenyl, $C_1-C_{12}$-alkylphenyl, $C_6H_5-CH=CH-$, $C_3-C_7$-cycloalkyl, $C_1-C_4$-alkoxyphenyl, $-CH_2-PO(OCH_3)_2$, $-CH_2-PO(OC_2H_5)_2$, $-CH_2-PO(OC_3H_7)$ or $-CH_2-PO(OC_4H_9)_2$ and $R^9$ is $C_1-C_{12}$-alkyl, phenyl or $C_1-C_{12}$-alkylphenyl and R' and R", which may be identical or different, are $C_1-C_4$-alkyl, 2-hydroxyethyl, $C_1-C_4$-alkoxyethyl, 2-phenoxyethyl, 2-chloroethyl, 2-cyanoethyl, 2-(carbomethoxy)-ethyl, 2-(carboethoxy)-ethyl, 2-(ethanoyloxy)-ethyl, 2-(propanoyloxy)-ethyl, allyl or benzyl, or R' is hydrogen or methyl and R" is phenyl which is unsubstituted or substituted by methyl, ethyl, methoxy or ethoxy, or is cyclohexyl, or

is N-pyrrolidinyl, N-piperidinyl or N-morpholinyl.

6. The dye as claimed in claim 5, wherein

R' and R" are methyl, ethyl, allyl, 2-hydroxyethyl, 2-(ethanoyloxy)-ethyl, 2-(propanoyloxy)-ethyl, 2-chloroethyl or benzyl or R' is methyl or hydrogen and R" is phenyl, 4-methylphenyl or 4-methoxyphenyl or

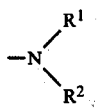

is pyrrolidinyl, piperidinyl or morpholinyl.

7. The dye as claimed in claim 5 or 6, wherein Y' is hydrogen, methyl, hydroxyl,

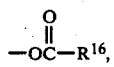

—NHCOR$^{10}$ or —NH—SO$_2$R$^{11}$, where R$^{10}$ is linear or branched C$_1$-C$_{12}$-alkyl, methoxymethyl, phenoxymethyl (which is unsubstituted or substituted by methoxy or C$_1$-C$_4$-alkyl), C$_3$-C$_7$-cycloalkyl, phenyl (which is unsubstituted or substituted by C$_1$-C$_4$-alkyl or C$_1$-C$_4$-alkoxy), benzyl, phenylethyl or C$_6$H$_5$—CH=CH—, R$^{11}$ is C$_1$-C$_{12}$-alkyl, phenyl or C$_1$-C$_{12}$-alkylphenyl and R$^{16}$ is C$_1$-C$_6$-alkyl or phenyl.

8. The dye as claimed in claim 5, wherein the radical

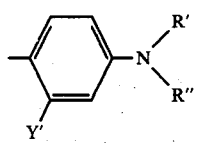

in the formula given is

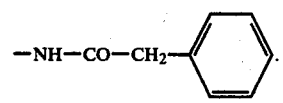

where
R$^{10}$ is linear or branched C$_1$-C$_{12}$-alkyl, methoxymethyl, phenoxymethyl (where phenoxy is unsubstituted or substituted by methoxy or C$_1$-C$_4$-alkyl), C$_3$-C$_7$-cycloalkyl, phenyl (which is unsubstituted or substituted by C$_1$-C$_4$-alkyl or C$_1$-C$_4$-alkoxy), benzyl, phenylethyl or C$_6$H$_5$—CH=CH—,
R$^{11}$ is C$_1$-C$_{12}$-alkyl, phenyl or C$_1$-C$_{12}$-alkylphenyl, R$^{12}$ is hydrogen, methyl, ethyl, methoxy or ethoxy and
R$^{13}$ is C$_1$-C$_6$-alkyl.

9. The dye as claimed in claim 5, wherein R' and R" are ethyl and Y' is —NH—COR$^8$ or —NH—SO$_2$R$^9$, where R$^8$ is C$_1$-C$_{12}$-alkyl or phenoxymethyl and R$^9$ is methyl or ethyl.

10. A dye as claimed in claim 5, wherein R' and R" are ethyl and Y' is

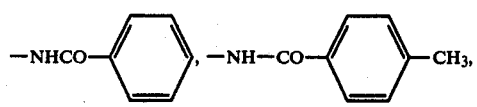

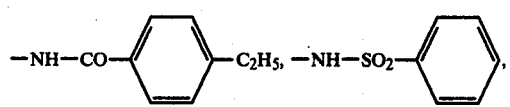

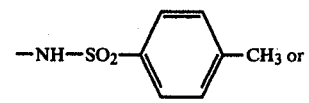

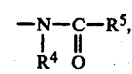.

11. A dye of the formula:

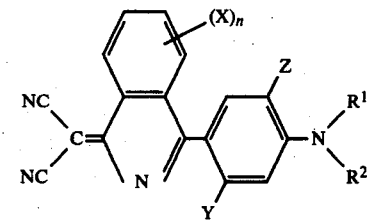

wherein
X is hydrogen, chlorine, C$_1$-C$_4$-alkyl or C$_1$-C$_4$-alkoxy, and if n is 2 the substituents may be identical or different,
n is 1 or 2,
R$^1$ is hydrogen, methyl, ethyl or 2-hydroxyethyl and R$^2$ is phenyl which is unsubstituted or substituted by C$_1$-C$_4$-alkyl or C$_1$-C$_4$-alkoxy, or is cyclohexyl, or
R$^1$ is hydrogen and
R$^2$ is C$_1$-C$_4$-alkyl or
R$^1$ and R$^2$ are C$_1$-C$_6$-alkyl; C$_1$-C$_4$-alkyl substituted by chlorine, cyano, hydroxyl, C$_1$-C$_4$-alkoxy, phenoxy, C$_2$-C$_5$-alkanoyloxy (which may or may not be substituted by C$_1$-C$_4$-alkoxy or phenoxy), or carbo-C$_1$-C$_4$-alkoxy; allyl; or phenyl-C$_1$-C$_4$-alkyl, or
—NR$^1$R$^2$ is a saturated heterocyclic five-membered or six-membered ring which may additionally contain an oxygen or an additional nitrogen as a ring member,
Y is $$-\underset{R^4}{\underset{|}{N}}-\underset{O}{\overset{\|}{C}}-R^5,$$

where $R^4$ is hydrogen or $C_1-C_4$-alkyl and $R^5$ is hydrogen, linear or branched $C_1-C_{12}$-alkyl, trifluoromethyl, chloromethyl, $C_1-C_4$-alkoxymethyl or phenoxymethyl (where phenoxy may or may not be substituted by one or two chlorine, methoxy, nitro or $C_1-C_4$-alkyl, and, in the case of two substituents, the substituents may be identical or different); phenylthiomethyl, where phenyl is unsubstituted or substituted by $C_1-C_4$-alkyl; benzyl; phenylethyl; $C_3-C_7$-cycloalkyl; phenyl which is unsubstituted or substituted by $C_1-C_{12}$-alkyl, $C_1-C_{12}$-alkoxy or nitro; $H_5C_6-CH=CH-$; or Y is N-$C_1-C_4$-alkylamino, when $R^1$ and $R^2$ are $C_1-C_4$-alkyl or Y is N,N-di-$C_1-C_4$-alkylamino, N-pyrrolidinyl, N-piperidinyl or N-morpholinyl when $$-N\begin{matrix}R^1\\R^2\end{matrix}$$

is N,N-di-$C_1-C_4$-alkylamino, N-pyrrolidinyl, N-piperidinyl or N-morpholinyl, and Z is hydrogen or, when $R^1$ and $R^2$ are $C_1-C_4$-alkyl or allyl and Y is $$-\underset{R^4}{N}-COR^5,$$

Z is hydrogen, methoxy or ethoxy.

12. The dye as claimed in claim 11 wherein Y is NH—$COR^8$, where $R^8$ is linear or branched $C_1-C_{12}$-alkyl, methoxymethyl, phenoxymethyl (where phenoxy is unsubstituted or substituted by methoxy or $C_1-C_4$-alkyl), phenylthiomethyl (where phenyl is unsubstituted or substituted by $C_1-C_4$-alkyl), benzyl, phenylethyl, phenyl, $C_1-C_{12}$-alkylphenyl, $C_6H_5-CH=CH-$, $C_3-C_7$-cycloalkyl, $C_1-C_4$-alkoxyphenyl.

13. The dye as claimed in claim 11 or 12 wherein $R^1$ and $R^2$ are $C_1-C_4$-alkyl, 2-hydroxyethyl, $C_1-C_4$-alkoxyethyl, 2-phenoxyethyl, 2-chloroethyl, 2-cyanoethyl, 2-(carbomethoxy)-ethyl, 2-(carboethoxy)-ethyl, 2-(propanoyloxy)-ethyl, 2-(ethanoyloxy)-ethyl, allyl or benzyl, the substituents $R^1$ and $R^2$ being identical or different, or $R^1$ is hydrogen or methyl and $R^2$ is phenyl which is unsubstituted or substituted by methyl, ethyl, methoxy or ethoxy, or is cyclohexyl, or $-NR^1R^2$ is pyrrolidinyl, piperidinyl or morpholinyl.

14. A dye of the formula:

wherein $R^{18}$ is methyl or ethyl.

15. A dye of the formula:

wherein $R^1$ and $R^2$ are both $C_1-C_6$ alkyl and $R^5$ is $C_1-C_{12}$ alkyl.

16. A dye of the formula where
$Y^1$ is $-NHCOR^8$,
$R^8$ is linear or branched $C_1-C_{12}$-alkyl, methoxymethyl, phenoxymethyl (where phenoxy is unsubstituted or substituted by methoxy or $C_1-C_4$-alkyl), phenylthiomethyl (where phenyl is unsubstituted or substituted by $C_1-C_4$-alkyl), benzyl, phenylethyl, phenyl, $C_1-C_{12}$-alkylphenyl, $C_6H_5-CH=CH-$, $C_3-C_7$-cycloalkyl, or $C_1-C_4$-alkoxyphenyl, and R' and R", which may be identical or different, are $C_1-C_4$-alkyl, 2-hydroxyethyl, $C_1-C_4$-alkoxyethyl, 2-phenoxyethyl, 2-chloroethyl, 2-cyanoethyl, 2-(carbomethoxy)-ethyl, 2-(carboethoxy)-ethyl, 2-(ethanoyloxy)-ethyl, 2-(propanoyloxy)-ethyl, allyl or benzyl, or R' is hydrogen or methyl and
R" is phenyl which is unsubstituted or substituted by methyl, ethyl, methoxy or ethoxy, or is cyclohexyl, or $-NR'R''$ is N-pyrrolidinyl, N-piperidinyl or N-morpholinyl.

17. The dye as claimed in claim 16, wherein
R' and R" are methyl, ethyl, allyl, 2-hydroxyethyl, 2-(ethanoyloxy)-ethyl, 2-(propanoyloxy)-ethyl, 2-chloroethyl or benzyl or R' is methyl or hydrogen and
R" is phenyl, 4-methylphenyl or 4-methoxyphenyl or $-NR^1R^2$ is pyrrolidinyl, piperidinyl or morpholinyl.

18. The dye as claimed in claim 16 or 17 wherein Y' is $-NHCOR^{10}$ where $R^{10}$ is linear or branched $C_1-C_{12}$-alkyl, methoxymethyl, phenoxymethyl (which is unsubstituted or substituted by methoxy or $C_1-C_4$-alkyl), $C_3-C_7$ cycloalkyl, phenyl (which is unsubstituted or substituted by $C_1-C_4$-alkoxy or $C_1-C_4$-alkyl), benzyl, phenylethyl or $C_6H_5-CH=CH-$.

19. The dye as claimed in claim 16, wherein the radical in the formula given is

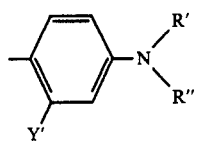

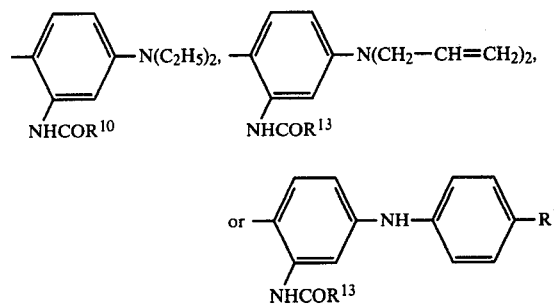

where

R¹⁰ is linear or branched $C_1$-$C_{12}$-alkyl, methoxymethyl, phenoxymethyl (where phenoxy is unsubstituted or substituted by methoxy or $C_1$-$C_4$-alkyl), $C_3$-$C_7$-cycloalkyl, phenyl (which is unsubstituted or substituted by $C_1$-$C_4$-alkyl or $C_1$-$C_4$-alkoxy), benzyl, phenylethyl or $C_6H_5$—CH=CH—, R¹² is hydrogen, methyl, ethyl, methoxy or ethoxy, and R¹³ is $C_1$-$C_6$-alkyl.

20. The dye as claimed in claim 16, wherein R' and R" are ethyl and Y' is —NH—COR¹⁸, where R¹⁸ is $C_1$-$C_{12}$-alkyl or phenoxymethyl.

21. The dye as claimed in claim 16, wherein R' and R" are ethyl and Y' is

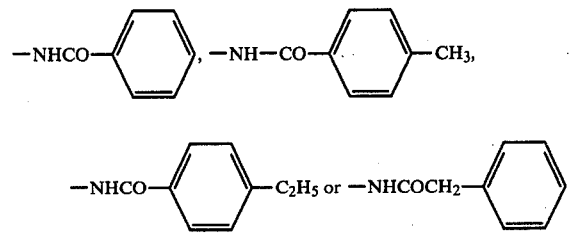

* * * * *